United States Patent [19]
Bell et al.

[11] Patent Number: 6,146,618
[45] Date of Patent: *Nov. 14, 2000

[54] DISAPPEARING COLOR SUNSCREEN COMPOSITIONS

[75] Inventors: Robert Bell, Miami; Denman Gray, Coral Springs, both of Fla.

[73] Assignee: IPA, LLC, Ft. Worth, Tex.

[*] Notice: This patent is subject to a terminal disclaimer.

[21] Appl. No.: 09/472,390

[22] Filed: Dec. 23, 1999

Related U.S. Application Data

[62] Division of application No. 09/129,938, Aug. 6, 1998, Pat. No. 6,007,797.

[51] Int. Cl.$^7$ .............................. A61K 7/42; A61K 7/44; A61K 7/00

[52] U.S. Cl. ............................ 424/59; 424/60; 424/400; 424/401

[58] Field of Search ............................... 424/59, 60, 400, 424/401

[56] References Cited

U.S. PATENT DOCUMENTS

| | | |
|---|---|---|
| 2,366,759 | 1/1945 | Thomas et al. . |
| 2,496,270 | 2/1950 | Coler . |
| 2,948,657 | 8/1960 | Siccama et al. . |
| 3,031,104 | 4/1962 | Moskovitz . |
| 3,042,263 | 7/1962 | Gallo, Sr. . |
| 3,152,731 | 10/1964 | Prussack . |
| 3,182,860 | 5/1965 | Gallo, Sr. . |
| 3,468,458 | 9/1969 | Leigh . |
| 3,751,563 | 8/1973 | Richardson . |
| 3,814,287 | 6/1974 | Darbon et al. . |
| 4,084,983 | 4/1978 | Bernhard et al. . |
| 4,271,984 | 6/1981 | Ducros et al. . |
| 4,818,491 | 4/1989 | Fariss . |
| 4,954,544 | 9/1990 | Chandaria . |
| 5,426,210 | 6/1995 | Kato et al. . |
| 5,523,075 | 6/1996 | Fuerst et al. . |
| 5,543,137 | 8/1996 | Repper et al. . |
| 5,562,896 | 10/1996 | Repper et al. . |
| 5,609,852 | 3/1997 | Galley et al. . |
| 6,007,797 | 12/1999 | Bell et al. ............................ 424/59 |

OTHER PUBLICATIONS

First Amended Complaint, IPA v Schering–Plough et al, Civil Action No. 98–482 (RRM), Jan. 22, 1999, 14 pages.
Defendants' Answer & Counterclaims to First Amended Complaint, IPA v Schering–Plough et al, Civil Action No. 98–482 (RRM), Feb. 19, 1999, 17 pgs.
Memorandum Opinion, Playtex Products, Inc. v. Schering–Plough, Civil Action No. 98–482–RRM, May 17, 1999, 38 pages.
Complaint–Jury Trial Demanded, Dec. 22, 1998, Playtex Products, Inc. v Schering–Plough, Civil Action No. 98–482 (RRM), 46 pages.
Declaration of Charles Fox, Playtex Products, Inc. v Schering–Plough, Civil Action No. 98–482 (RRM), Oct. 15, 1998, 10 pages.
Declaration of John M. Clayton, Playtex Products, Inc. v Schering–Plough, Civil Action No. 98–428 (RRM), Oct. 16, 1998, 16 pages.
Trial Transcript Mar. 2, 1999 (Excerpts) vol. A, Playtex Products, Inc. v Schering–Plough, Civil Action No. 98–482, 42 pages.
Trial Transcript Mar. 3, 1999 (Excerpts) vol. A, Playtex Products, Inc. v Schering–Plough, Civil Action No. 98–482, 33 pages.
Photocopy, Crayola Craft fabric and craft paint, 1992.
Deposition Transcript of Jack Katz, Feb. 10, 1999, pp. 1–32, regarding civil action entitled, Playtex Products, Inc. and Sun Pharmaceuticals Corporation vs. Schering–Plough Healthcare Products, Inc., Case No. 98–482–RPM, United States District Court, Middle District of Delaware.
Photocopy, Lucky Kentucky Moisturizing Balm, 1974.
Article: Gleams Notions, by Harvey M. Fishman, "happi", Jan. 1995, p. 28.
Article: Formulating Color Cosmetics Worldwide, by Lou Caivo, Estee Lauder, New York, USA, 4 pages, Mar., 1994.
Product Alert Apr. 12, 1993, Defendant's Exhibit 30.
Plaintiff's Trial Exhibits 26, 27, 28, 38, 41, 42, 43, 44, 138, 142, 144, 146, 186, 187, 188, 216, 217, 218, (42 pages), 1995.
Photocopy, PreSun for Kids, 1 page, 1995.
Photocopy, Bain de Soleil Kids, 1 page, 1995.
Photocopy, L'Oreal Plenitude, 2 pages, 1995.
Photocopy, Plenitude Active Daily Moisture Lotion, 5 pages, 1995.
Photocopy, Oil of Olay, 2 pages, 1991.
Photocopy, Oil of Olay Daily UV Protectant Beauty Fluid, 6 pages, 1995.
Photocopy, Australian Gold SPF 15, 2 pages, 1995.
Photocopy, Duane Reade, Skin Selects Sun Protecting Lotion, 3 pages, 1995.
Photocopy, Coppertone Skin Selects, Sun Protecting Lotion, 2 pages, 1995.
Photocopy, Harmon FACES only, 3 pages, 1995.

(List continued on next page.)

*Primary Examiner*—Shelley A. Dodson
*Attorney, Agent, or Firm*—Duft, Graziano & Forest PC

[57] ABSTRACT

Sunscreens are colored with oil-soluble dyes approved for use in skin care products (such as sunscreens, lotions, etc.). The color imparted by the dyes substantially disappears shortly after the sunscreen emulsion is applied to skin. This colored sunscreen emulsion includes a oil-soluble phase, at least one sunscreen active agent, water, and an emulsifier. The oil-soluble phase comprises from about 0.0005 to about 0.5 percent by weight of the complete emulsion of at least one oil-soluble dye. The dye imparts a color other than white to the sunscreen emulsion.

The sunscreen active ingredient is provided in an amount effective to protect against the actinic radiation of the sun. Sufficient water is provided to form the colored emulsion. The emulsion additionally contains at least one emulsifier in an amount effective to provide an at least substantially stable emulsion. Other optional ingredients may also be compounded into the sunscreen formulations.

25 Claims, No Drawings

OTHER PUBLICATIONS

Photocopy, FACES only, 2 pages, 1995.
Photocopy, Australian Gold SPF 15 (front), 1 page, 1995.
Photocopy, Australian Gold 15 (back) 2 pages, 1995.
Article: Precise Color Communication, Minolta Publication, Defendant's Trial Exhibit 48, 4 pages, 1995.
Article: Practical Color Measurement, by Anni Berger–Schunn, A Wiley–Interscience Publication, Plaintiff's Trial Exhibit No. 143, 15 pages, 1994.

Photocopy, Artmatic USA Cosmetics, Instruction and Ingredient Label, 1 page, 1995.

US–A–3 964 832 (N.B. Cohen)—Abstract Figure (From European Search Report dated Nov. 23, 1989).

European Search Report, dated Nov. 23, 1989, Examiner Girard, Y.A.

Photocopy, Banana Boat Aloe Vera Body Lotion, 1995.

DISAPPEARING COLOR SUNSCREEN COMPOSITIONS

This application claims the benefit of Division of Ser. No. 09/129,938 filed Aug. 6, 1998, now U.S. Pat. No. 6,007,797.

CROSS-REFERENCE TO RELATED APPLICATIONS

None

STATEMENT REGARDING FEDERALLY SPONSORED RESEARCH OR DEVELOPMENT

Not Applicable.

BACKGROUND OF THE INVENTION

Sunscreens are substances or compositions applied to the skin to protect the skin from sunburn caused by the sun's ultraviolet rays. When uniformly applied to the body, sunscreens can be highly effective in protecting against sunburn. However, sunscreen failure can occur when areas of the body are missed because the sunscreen is hard to see or visualize after being applied or rubbed onto the skin. Children are at greater risk of sunburn than adults, since coverage on children's skin tends to be more incomplete, uneven or inconsistent.

U.S. Pat. No. 5,747,011 was issued to Ross et al. and assigned to Schering-Plough HealthCare Products, Inc. This patent is hereby incorporated herein by reference in its entirety. This patent discloses a colored, sunscreen emulsion which employs a water-soluble dye or a blend of water-soluble dyes. The color imparted by the dyes is said by this patent to substantially disappear when the sunscreen emulsion dries after it is spread on the skin and/or is rubbed out. The coloration in the sunscreen is said to enable the user to more effectively protect against sunburn by allowing more complete and uniform coverage of the sunscreen on the skin.

The sunscreen emulsion disclosed in the Ross et al. patent includes at least one water-soluble dye that imparts a color other than white to the sunscreen emulsion, such that when the sunscreen emulsion dries after it is spread on the skin and/or is rubbed out, the color is said to substantially disappear. Various water-soluble dyes are listed in the patent as useful. The Ross et al. patent specifically discloses that oil-soluble dyes tend to stain the skin (see col. 2, lines 39–42), and thus indicates that they should not be used in a colored sunscreen that is intended to at least substantially lose its color upon or shortly after application to the skin.

BRIEF SUMMARY OF THE INVENTION

The present inventors have discovered that oil-soluble colors approved for use in skin care products (such as sunscreens, lotions, etc.) can be added to the oil phase of a sunscreen to provide the disappearing color feature described above. This colored sunscreen emulsion comprises a oil-soluble phase, at least one sunscreen active agent, water, and an emulsifier.

The oil-soluble phase comprises from about 0.0005 to about 0.5 percent by weight of the complete emulsion of at least one oil-soluble dye. The dye imparts a color other than white to the sunscreen emulsion, as sold. Surprisingly, when the sunscreen emulsion is spread on skin and/or is rubbed into skin, the color substantially disappears.

The sunscreen active ingredient is provided in an amount effective to protect against the actinic radiation of the sun to a degree, as defined by its sun protection factor (SPF). Sufficient water is provided to form the colored emulsion. The emulsion additionally contains at least one emulsifier in an amount effective to provide an at least substantially stable emulsion.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims.

Oil-Soluble Dyes

The oil-soluble dyes contemplated for use in the present invention are any one or more dyes, approved now or in the future for use in topically-applied compositions, that are soluble in the water-insoluble phase of a sunscreen composition in an amount effective to provide a desired color. Exemplary of these oil-soluble dyes are the following:

D&C Green #6

D&C Red #12

D&C Violet #2

D&C Yellow #11

One or more oil-soluble dyes are used in an amount effective to provide a desired hue and color intensity in a sunscreen. While water-soluble dyes may also be used in the present compositions, at least one water-insoluble dye characterizes the compositions of the present invention. The oil-soluble dye is used as from about 0.0005 to about 0.5 percent by weight, alternatively from about 0.002 to about 0.2 percent by weight, alternatively from about 0.01 to about 0.2 percent by weight of the complete emulsion. The minimum amount of dye is unlimited, though preferably a perceptible color change to the composition will be provided. The maximum amount of dye is limited to that amount which leaves the wearer's skin an aesthetically acceptable color. Desirably, the maximum amount of dye is small enough not to leave perceptible non-natural coloration. Residual coloration resembling tanned human skin (i.e. sunless tanning action) may be provided, however, within the scope of the invention.

The oil-soluble phase, sunscreen active agents, emulsifier, and other sunscreen ingredients can be materials conventionally used in sunscreen compositions and known to those skilled in the art, used in amounts conventionally used in sunscreen compositions. Examples of these and other useful ingredients can be found in U.S. Pat. No. 5,747,011 (incorporated by reference above), U.S. Pat. Nos. 5,208,011 and 4,522,807 (hereby incorporated herein by reference in their entireties), other patents and published references, CTFA Cosmetic Ingredient Dictionary, published by the Cosmetic, Toiletry and Fragrance Association, Inc., 1110 Vermont Avenue, NW, Wash. D.C. 20005, Third Edition 1982, and other sources of information available to persons skilled in the art. Specific ingredients contemplated for use herein are the following:

Sunscreen Actives

The compositions of the present invention can contain a sunscreening effective amount of one or more oil-soluble or water-soluble sunscreening UV-B actives or a mixture of one or more UV-B actives and one or more UV-A actives.

UV-A type sunscreening actives protect against long wavelength actinic radiation of the sun in the 320 to 400 nm range and UV-B type sunscreening actives protect against shorter wavelength, actinic radiation of the sun in the 290–320 nm range.

The compositions contemplated herein comprise from about 1% by weight to about 50% by weight, preferably from about 1% to about 33% by weight, of sunscreen-active ingredients. The present composition may desirably contain opaque sunscreens, such as zinc oxide or titanium dioxide, which function by providing an opaque barrier to UV light. The present composition may desirably contain colored substances which attenuate light, such as red petrolatum. The preferred compositions contain one or more of the following sunscreens, which function by selectively absorbing ultraviolet light having wavelengths which are responsible for tanning or burning skin.

- octocrylene
- 2-ethylhexyl salicylate;
- 2-ethoxyethyl-p-methoxycinnamate;
- 2-ethylhexyl-p-methoxycinnamate (also known as octyl methoxycinnamate);
- 2-[bis(2-hydroxyethyl)-amino]ethyl salicylate;
- hydroxyethylaminoethyl-p-methoxycinnamate;
- pentyl 4-dimethylaminobenzoate;
- octyl dimethyl p-aminobenzoic acid;
- pentyl dimethyl p-aminobenzoic acid;
- ethyl dihydroxypropyl p-aminobenzoic acid;
- 2-hydroxy-1,4-naphthoquinone;
- 3,3,5-trimethylcyclohexyl salicylate;
- 2-ethylhexyl-2-cyano-3,3-diphenyl acrylate;
- ethyl 4-[bis(2-hydroxypropyl)amino]benzoate;
- digalloyl trioleate;
- menthyl anthranilate;
- salicylic acid 3,3,5-trimethyl ester (commonly known as homomenthyl salicylate or homosalate);
- glyceryl-p-aminobenzoate;
- p-aminobenzoic acid;
- isobutyl-p-aminobenzoate;
- isoamyl-p-dimethylaminobenzoate;
- 2-hydroxy-4-methoxybenzophenone-5-sulfonic acid;
- 2-phenylbenzimidazole-5-sulfonic acid;
- 2-2-dihydroxy-4-methoxybenzophenone;
- 2-hydroxy-4-methoxybenzophenone (commonly called oxybenzone);
- butylmethoxydibenzoylmethane (also known as avobenzone and sold under the trade name PARSOL 1789);
- benzophenone-8;
- benzophenone-4;
- benzophenone-3;
- 4-mono(3-hydroxypropyl)amino isomer of ethyl benzoate;
- 4-bis(3-hydroxypropyl)amino isomer of ethyl benzoate;
- 2-ethylhexyl-p-dimethylaminobenzoate;
- sulfomethyl benzylidene bornanone;
- urocanic acid and its esters; and mixtures thereof.

New sunscreens which may be discovered in the future may also be used within the scope of the present invention.

Typical sunscreen actives include para-aminobenzoic acid up to about 15 weight percent or from about 5 to 15% in admixture with other sunscreen actives; cinoxate up to about 3 weight percent or about 1 to 3% in admixture; diethanolamine methoxycinnamate up to 10 weight percent or about 8 to 10% in admixture; digalloyl trioleate up to 5 weight percent or about 2 to 5% in admixture; dioxybenzone up to 3 weight percent alone or in admixture; ethyl 4-[bis (hydroxypropyl)]aminobenzoate up to 5 weight percent or about 1 to 5% in admixture; glyceryl aminobenzoate up to 3 weight percent or about 2 to 3% in admixture; homosalate up to 15 weight percent or about 4 to 15% in admixture; lawsone up to 0.25 weight percent with dihydroxyacetone up to 3 weight percent, or in admixture 0.25 weight percent lawsone and 3 wt. % dihydroxyacetone; menthyl anthranilate up to 5 weight percent or about 3.5 to 5% in admixture; octocrylene up to 10 weight percent or 7 to about 10% in admixture; octyl methoxycinnamate up to 7.5 weight percent or about 2 to 7.5% in admixture; octyl salicylate or 2-ethylhexyl salicylate up to 5 weight percent or about 3 to 5% in admixture; oxybenzone up to 6 weight percent or about 2 to 6% in admixture; padimate "O" up to 8 weight percent or about 1.4 to 8% in admixture; phenylbenzimidazole sulfonic acid up to 4 weight percent or about 1 to about 4% in admixture; red veterinary petrolatum up to 95 percent or about 30 to 95% in admixture; sulisobenzone up to 10 weight percent or about 5 to 10% in admixture; titanium dioxide up to 25 weight percent or about 2 to 25% in admixture; and triethanolamine salicylate up to 12 weight percent or about 5 to 12% in admixture.

Typical suitable UV-B type sunscreening actives include benzophenone-3, benzophenone-8, p-methoxycinnamate, substituted para-aminobenzoates, e.g.,alkyl (e.g. 2-ethylhexyl) esters of para-methoxycinnamate, octyl methoxycinnamate and octyl para-methoxycinnamate, available from Givaudan Corp., Clifton, N.J. 07104 under the tradename Parsol MCX and usually present in the range of about 2 to 7.5 weight percent, ethylhexyl or octyl salicylate available from Harmann and Riemer, Springfield, N.J., 07081, usually in the range of about 3 to 5 weight percent. The amount of UV-B type sunscreening active should be sufficient to give an SPF of at least 2 to 15.

Typical suitable UV-A type sunscreening actives include oxybenzone, usually in the range of about 2 to about 6 weight percent. Sunscreen emulsions containing mixtures of UV-B and UV-A type sunscreen actives should be sufficient to provide an SPF of 2 to 50.

Emulsifiers and Emulsions

A stable emulsion is a mixture of two immiscible liquids, i.e. liquids that are not mutually soluble, but in the presence of an emulsifier, are mechanically agitated and shaken so thoroughly together that one liquid forms drops in the other one, giving the mixture the appearance of a homogeneous liquid. Liquids can include materials which are solid or solid-like at room temperature, but will liquefy at a higher temperature during processing. The presence of an emulsifier enables one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with nonpolar and polar parts that are able to reside at the interface of the two immiscible liquids. As used herein in reference to the water-in-oil emulsifiers, the term "HLB value" means the hydrophile/lipophile balance. The HLB value has been used by those skilled in the emulsion art for selecting emulsifiers useful for preparing, inter alia, water-in-oil emulsions. See U.S. Pat. No. 4,177,259 and references cited therein.

An "at least substantially stable emulsion" as defined herein is an emulsion which remains as one bulk phase (without visible separation to the naked eye) for a period of at least 24 hours without any effort being made to redisperse its ingredients.

The sunscreen emulsions of the present invention typically comprise from about 35% to about 96%, preferably from about 55% to about 85%, of an aqueous phase and from about 4% to about 65%, preferably from about 15% to about 45%, of a water insoluble phase. In the present disclosure, the percentage of any adjuvant or phase is based on the weight of the entire composition. The present emulsions contain the water insoluble phase and the aqueous phase in amounts effective to provide a stable emulsion having activity as a sunscreen.

Some ingredients predominantly reside in the aqueous phase, other ingredients predominantly reside in the water insoluble phase, still other ingredients reside in the interface between the phases, and some ingredients are partitioned between the two phases or are found in an additional phase of the present emulsion. Thus, an indication herein that an ingredient resides in a certain phase is not an exclusion of that ingredient from other phases of the present emulsions.

An oil-in-water (o/w) emulsion is a mixture where oil droplets (the discontinuous phase) are dispersed in water (a continuous aqueous phase). A water-in-oil (w/o) emulsion is a mixture where water droplets (the discontinuous phase) are dispersed in oil (a continuous oil phase). Preferably the composition of the present invention is an oil-in-water emulsion where the oil-soluble actives are dispersed in the oil phase, prior to mixture with the water phase. The type of emulsion, oil-in-water (o/w) or water-in-oil (w/o) formed, is sometimes determined by the volume ratio of the two liquids provided the ratio is sufficiently high. For example, with 5% water and 95% oil (an o/w phase ratio of 19), the emulsion likely will become w/o. For moderate ratios (<3), the type of emulsion is decided by several factors, such as order of addition or type of emulsifier. One liquid slowly added to a second liquid with agitation usually results in the second liquid being the continuous phase. Another factor is preferred solubility of the emulsifier, the phase in which the emulsifier is soluble most probably is continuous.

More complex emulsions such as double emulsions are formed where an emulsion is dispersed in an continuous phase. For example, in an oil in-water-in oil (o/w/o) emulsion, the water in a continuous water phase containing dispersed oil droplets, are themselves dispersed in a continuous oil phase. Similarly, in a water-in oil-in water (w/o/w) emulsion, the oil in a continuous phase containing dispersed water droplets, are themselves dispersed in a continuous water phase. These more complex emulsions find use as a system for slow delivery, extraction, etc.

The sunscreen emulsions of the present invention comprise from about 35% to about 96%, preferably from about 55% to about 85%, of an aqueous phase and from about 4% to about 65%, preferably from about 15% to about 45%, of a water insoluble phase. In the present disclosure, the percentage of any adjuvant or phase is based on the weight of the entire composition. The present emulsions contain the water insoluble phase and the aqueous phase in amounts effective to provide a stable emulsion having activity as a sunscreen.

Typical suitable emulsifiers having an HLB value about 1 to about 7 include sorbitan monooleate, sorbitan sesquioleate, sorbitan isostearate, sorbitan trioleate, PEG-22/dodecyl glycol copolymer, PEG-45/dodecyl glycol copolymer, polyglyceryl-3-diisostearate, polyglycerol esters of oleic/isostearic acid, polyglyceryl-6 hexaricinolate, polyglyceryl-4 oleate, polyglyceryl-4 isostearate, polyglyceryl-4 oleate/PEG-8 propylene glycol cocoate, oleamide DEA, sodium glyceryl oleate phosphate and hydrogenated vegetable glycerides phosphate.

Other emulsifiers useful in the present invention may be non-ionic, liquid or solid at room temperature and preferably compatible, i.e., soluble and stable with emollients. Preferred emulsifiers have a HLB value of less than about 5, e.g., sorbitan sequioleate (HLB value is 3.7), sorbitan monooleate (HLB value is 4.3) and sorbitan trioleate (HLB value is 1.8). Other preferred emulsifiers include polymeric emulsifiers such as copolymers of C10–C30 alkyl acrylates and one or more monomers of acrylic acid or methacrylic acid, also known as Pemulen Registered TM TR1 and TR2, trademark of B.F. Goodrich Inc., Cincinnati, Ohio. Other emulsifiers include sorbitan esters such as sorbitan isostearate available as Crill 6, tradename of Croda Inc. of New York, N.Y.; polyglyceryl-3 distearate available as Cremophor, tradename of tradename of BASF, Parsippany N.J.; and carbomer, which is a homopolymer of acrylic acid crosslinked with an alkyl ether of sucrose, available as Carbopol 941, tradename of B.F. Goodrich, Cleveland, Ohio; and surfactants such as such as DEA-cetyl phosphate, also known as Amphisol Registered TM, trademark of Bernel Chemical Co., Englewood, N.J. Still other emulsifiers include cetyl dimethicone copolyol, cetyl dimethyl copolyol, During preparation of the emulsion, an acid or a base may be added to adjust the pH of one or more ingredients, e.g. to adjust the viscosity of a polymeric thickener, prior to its inclusion in the sunscreen composition. For example, triethanolamine, a base, can be used to increase the pH of the water phase and consequently, modify the desired viscosity of the emulsion.

The sunscreen can have a pH of about 6.5 to about 8, preferably from about 6.5 to about 7.5, more preferably the pH of the sunscreen is neutral, i.e. about 7.0.

Conveniently, one or more emulsifiers can be used in the compositions of the present invention in amounts ranging from about 0.05 to about 20 weight percent of emulsion, preferably from about 0.1 to about 15%, more preferably from about 5 to about 10%.

Film-Forming Polymers

Water-insoluble film-forming polymers can be added to the composition to provide a matrix or binder which physically envelops the sunscreen with the aid of the oil-soluble solubilizer, preventing the sunscreen from being absorbed by the skin. The polymers also prevent the sunscreen from being rubbed off by physical contact with clothing, towels, furniture, other parts of the body (e.g. scratching the protected area), etc. Specific polymers contemplated for use herein include the following:

aliphatic alkenes, for example, polyethylene, oxidized polyethylene, polybutene, polypropylene, or their copolymers;

copolymers of vinyl chloride and maleic acid or anhydride;

alkyl polyvinyl pyrrolidones, such as copolymers of polyvinyl pyrrolidone with eicosene or dodecene;

acrylic resins;

methacrylic resins; and mixtures thereof.

Each said polymer can have a carbon chain length of from about 50 to about 5000 carbon atoms.

Other polymers contemplated for use herein are those mentioned in U.S. Pat. Nos. 3,666,732 (polymers of p-aminobenzoic acid and its derivatives, and their copolymers with acrylic, methacrylic, itaconic, or crotonic acids, alkyl esters, and hydroxyalkyl esters); 3,666,732 (polyalkene resins); and 3,751,563 (polyalkene resins). The disclosures of polymers in the U.S. patents listed in the preceding sentence are hereby incorporated herein by reference. Other water-insoluble polymers which have utility in skin-contacting cosmetics are also contemplated for use herein. The present compositions optionally contain from about 1.5% to about 12.5% of one or more such polymers.

Oil-Soluble Solubilizer

The water insoluble phase of the present emulsion further optionally comprises at least one oil-soluble solubilizer having a cohesive energy between about 80 and about 150 calories per cc., preferably from about 100 to about 115 calories per cc. The aggregate cohesive energy of all the oil-soluble solubilizers used in a particular composition is also preferably from about 100 to about 115 calories per cc. The cohesive energy of a material is defined in Chapter 2.1 of A.F.M. Barton, CRC Handbook of Solubility Parameters and Other Cohesion Parameters, CRC Press, Inc., Boca Raton, Fla. (19183). The composition optionally contains from about 0.1% to about 15% of such solubilizers. Oil-soluble solubilizers give the present sunscreen compositions, and particularly the films resulting from their application, a greater affinity for skin. Oil-soluble solubilizers also function as plasticizers for the polymer vehicles described above, so the film of the sunscreen composition will be mobile enough to form a thin layer on the wearer's skin and flexible enough to conform closely to the wearer's skin during use.

Specific oil-soluble solubilizers contemplated herein include the following:

aliphatic lactates of fatty acids having from about 12 to 20 carbon atoms, for example, myristyl lactate;

Guerbet alcohols;

fatty alcohols having from 6 to 22 carbon atoms, such as stearyl alcohol or a mixture of fatty alcohols;

dialkyl maleates;

alkyl ricinoleates;

alkyl hydroxystearates;

alkyl acetyl ricinoleates;

nonionic surfactants having HLB's between 1 and about 5;

alkyl salicylates such as octyl salicylate;

and mixtures thereof.

("Alkyl" is defined herein generally to include straight or branched chain alkyl having from 1 to about 22 carbon atoms.) Exemplary nonionic surfactants useful herein include lanolin alcohols, glycerol monooleate, and sorbitan esters of fatty acids (such as sorbitan stearate and sorbitan oleate).

Another optional ingredient of the water insoluble phase is from about 0.1 to about 10% by weight of alkoxylated castor oil, more broadly defined as consisting essentially of alkoxylated ricinolein. From 1 to 100 moles of an alkylene oxide (preferably ethylene oxide), preferably from about 5 to about 40 moles of ethylene oxide, may be combined with each molecule of ricinolein. Mixtures of alkoxylated castor oils having different amounts or kinds of alkylene oxide content are also contemplated for use herein.

Water-Insoluble Antioxidants

Antioxidants such as tocopherol may be used in the water insoluble phase

Water

Water is employed in amounts effective to form the emulsion. For hydrophilic or water-loving ingredients, e.g., emulsifiers, emolients, etc., the amount of water should be sufficient to at least solubilize these ingredients. For hydrophobic or water-repelling ingredients, the water should be employed in amounts to serve as the continuous phase of the emulsion, at least for oil-in water emulsions. Thus, amount of water in the emulsion or composition can range from about 2 to 95 weight %, preferably from 50 to 85%. Deionized water may optionally be used.

Emollients

An emollient is an oleaginous or oily substance which helps to smooth and soften the skin, and may also reduce its roughness, cracking or irritation. Typical suitable emollients include mineral, oil, having a viscosity in the range of 50 to 500 centipoise (cps), lanolin oil, coconut oil, cocoa butter, olive oil, almond oil, macadamia nut oil, aloe extracts such as aloe vera lipoquinone, aloe vera gel, synthetic jojoba oils, natural sonora jojoba oils, safflower oil, corn oil, liquid lanolin, cottonseed oil and peanut oil.

Other suitable emollients and adjuvants include squalane, castor oil, polybutene, odorless mineral spirits, sweet almond oil, avocado oil, calophyllum oil, ricin oil, vitamin E acetate, olive oil, silicone oils such as dimethylpolysiloxane and cyclomethicone, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa., capric triglyceride, caprylic triglyceride, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at ambient temperatures may be use in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the sunscreen emulsion in an amount ranging from about 10 to about 50 weight %, preferably about 20 to about 40%.

Humectants

A humectant is a moistening agent that promotes retention of water due to its hygroscopic properties. Suitable humectants include glycerin, polymeric glycols such as poyethylene glycol and polypropylene glycol, and sorbitols such as sorbitol solution. One or more humectants can optionally be included in the in the sunscreen in amounts from about 1 to 10 weight %.

Dry-Feel Modifier

A dry-feel modifier is an agent which when added to a emulsion, imparts a "dry feel" to the skin when the emulsion dries. Dry-feel modifiers may also reduce sunscreen migration on the skin. Dry feel modifiers can include starches, talc, kaolin, chalk, zinc oxide, silicone fluids, inorganic salts such as barium sulfate and sodium chloride, $C_6$ to $C_{12}$ alcohols such as octanol; sulfonated oils; surface treated silica, precipitated silica, fumed silica such as Aerosil Registered TM available from the Degussa Inc. of New York, N.Y. or mixtures thereof; dimethicone, a mixture of mixture of methylated linear siloxane polymers, available as DC200 fluid, tradename of Dow Corning, Midland, Mich. One or more dry-feel modifiers can optionally be included in the sunscreen in amounts ranging from 0.01 to about 20 weight %, preferably from about 0.5 to about 6 weight %.

Waterproofing Agents

A waterproofing agent is a hydrophobic material that imparts film forming and waterproofing characteristics to an emulsion. Typical suitable waterproofing agents include copolymers derived from polymerization of octadecene-1 and maleic anhydride in accordance with the published procedures such as those in U.S. Pat. No. 3,860,700 and Reissue No. 28,475. A preferred waterproofing agent is a polyanhydride resin, also known as PA-18, tradename of the Chevron Chemicals Co., San Francisco, Calif. Another preferred waterproofing agent is a copolymer of vinyl pyrollidone and eicosene monomers such as Ganex Polymer, tradename of ISP Inc. of Wayne, N.J. Another suitable waterproofing agent is dimethicone.

By the term "waterproofing effective amount of at least one waterproofing agent" means the waterproofing agent(s) is used in amounts effective to allow the sunscreen to remain on the skin after exposure to circulating water for at least 80 minutes using the procedures described in "Sunscreen Drug Products for OTC Human Use", Federal Register, Vol. 43, Aug. 25, 1978, Part 2, pp 38206–38269. One or more waterproofing agents can optionally be included in the sunscreen composition in an amount ranging from about 0.01 to about 10.0 weight percent, preferably about 1.0 to about 10.0 percent.

Antimicrobial Preservative

An antimicrobial preservative is a substance or preparation which destroys, prevents or inhibits the multiplication/growth of microorganisms in the sunscreen composition and may offer protection from oxidation. Preservatives are used to make self-sterilizing, aqueous based products such as emulsions. This is done to prevent the development of microorganisms that may be in the product from growing during manufacturing and distribution of the product and during use by consumers who may inadvertently contaminate the products during normal use. Typical preservatives include the lower alkyl esters of para-hydroxybenzoates (parabens) especially, methylparaben, propylparaben, isobutylparaben and mixtures thereof, benzyl alcohol and benzoic acid, or imidazolidinyl urea. One or more antimicrobial preservatives can optionally be included in the sunscreen composition in an amount ranging from about 0.001 to about 10 weight percent, preferably about 0.05 to about 2 percent.

Antioxidants

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA)(usually as a mixture of ortho and meta isomers), butylated hydroxytoluene (BHT), nordihydroguaiaretic acid, vitamin E, vitamin E acetate, vitamin C and alkylated parabens such as methylparaben and propylparaben. One or more antioxidants can optionally be included in the sunscreen composition in an amount ranging from about 0.001 to about 5 weight percent, preferably about 0.05 to about 2 percent.

Chelating Agents

Chelating agents are substances used to chelate or bind metallic ions with a certain heterocylic ring structure so that the ion is held by chemical bonds from each of the participating ring. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.1 weight percent.

Other Adjuvants

Some other adjuvants which may be employed are counterirritants such as allantoin, plant extracts such as chamomile extract, vitamins such as Vitamin E, Vitamin K1, Vitamin A, Vitamin B's, Vitamin C, etc., electrolytes such as sodium chloride, fatty acids such as stearic acid, etc.

Fragrances

Fragrances are aromatic compounds which can impart an aesthetically pleasing aroma to the sunscreen composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the sunscreen composition in an amount ranging from about 0.001 to about 10 weight percent, preferably about 0.05 to about 5 percent.

Leveling Agents

The emulsion can contain leveling agents, which are ingredients dispersed in the emulsion to assist the application of a uniform film of the composition on the skin. From 0 to about 5%, preferably from 0 to about 3.5%, of the composition may be a leveling, agent. Exemplary leveling, agents are silica, clays or earths, titanium dioxide, mica, and zinc oxide. The leveling agent can also be added in larger amounts to function as an opaque barrier layer.

Propellants

Propellants may be blended into the composition to facilitate delivery of the sunscreen in aerosol form, using conventional aerosol technology.

Miscellaneous Ingredients

Although an attempt has been made to give many examples of suitable ingredients, the foregoing listing is not exhaustive. The incorporation of any listed or unlisted ingredients in any amount, great or small, which does not destroy the utility of the composition as a sunscreen is expressly contemplated herein.

Dispensers

The sunscreen emulsions of the present invention containing the disappearing color indicator can be stored or dispensed in any container suitable for convenient delivery, i.e. pouring or spraying. Such containers can include but are not limited to tubes, jars, bottles, lotion pumps, pump spray bottles and aerosols.

WORKING EXAMPLES

The following working examples are provided for specific guidance on how to make and use the present compositions. The provision of specific examples in no way limits the full scope of the invention as presently disclosed and claimed. The inventors contemplate that the present invention can be carried out using a variety of different sunscreen compositions, by adding a suitable quantity of an oil-soluble dye to the composition.

Example 1

A water-in-oil sunscreen emulsion composition is made as follows. An emulsifier or water-insoluble phase is prepared by blending, at room temperature, cetyl dimethicone copolyol, polyglyceryl-3-distearate, polyglyceryl-4 isostearate, cetyl dimethyl copolyol, hexyl laurate, caprylic and/or capric triglyceride, propylparaben, methylparaben, p-methoxycinnamate, ethylhexyl salicylate, oxybenzone, minor ingredients, and about 0.12% by emulsion weight of a color blend of D&C Green #6, D&C Red #12, and D&C Violet #2 in suitable proportions to make a purple emulsion.

Separately, an aqueous phase is prepared by combining, at room temperature, deionized water, aloe vera gel, sodium chloride, chamomile extract, ascorbic acid (Vitamin C), and minor ingredients.

The two phases are then combined by adding the water phase to the emulsifier phase with constant mixing. The mixture is then homogenized with a suitable homogenizing mill until the required viscosity is reached.

The resulting sunscreen is applied to human skin and rubbed in well, as sunscreens are conventionally applied. The sunscreen is initially purple. As it is rubbed in the color fades, then essentially disappears, leaving the treated skin a normal skin color.

Example 2

Example 1 is repeated, but substituting for the color blend of that example a color blend of D&C Green #6 and D&C Yellow #11 in proportions suitable to make a green emulsion. Use of the emulsion as a sunscreen is demonstrated, with essentially the same result.

Example 3

Sea & Ski Kids Color Sun Block (SPF 30) is modified by adding to it the color blend of Example 1. Use of the emulsion as a sunscreen is demonstrated, with essentially the same result.

What is claimed is:

1. A colored sunscreen composition for application to human skin, comprising:
    a sunscreen active to protect the skin from ultraviolet radiation;
    an oil-soluble dye to impart a color, other than white, to the composition;
    and water, wherein application of the composition to the skin imparts the color to the skin and wherein the color substantially disappears when the composition is rubbed and/or spread onto the skin.

2. A composition according to claim 1, wherein the dye comprises one of the following:
    D&C Green $6, D&C Red #12, D&C Violet #2, D&C Yellow #11, and mixtures thereof.

3. A composition according to claim 1, wherein the dye comprises about 0.0005 to about 0.5 percent by weight of the composition.

4. A composition according to claim 1, wherein the dye comprises about 0.002 to about 0.2 percent by weight of the composition.

5. A composition according to claim 1, wherein the sunscreen active comprises UV-A active, UV-B active, and mixtures thereof.

6. A composition according to claim 1, wherein the active comprises between about 1% to 50% by weight of the composition.

7. A composition according to claim 6, wherein the active comprises between about 1% to 33% by weight of the composition.

8. A composition according to claim 1, wherein the active comprises one of zinc oxide or titanium dioxide.

9. A composition according to claim 1, further comprising an emulsifier to provide a the composition with a substantially stable emulsion.

10. A composition according to claim 9, wherein the emulsifier comprises an oil-in-water emulsifier.

11. A composition according to claim 9, wherein the emulsifier comprises an water-in-oil emulsifier.

12. A composition according to claim 1, further comprising a film-forming polymer.

13. A composition according to claim 1, further comprising an oil-soluble solubilizer.

14. A composition according to claim 1, further comprising a water-insoluble antioxidant.

15. A composition according to claim 1, further comprising an emollient.

16. A composition according to claim 1, further comprising a humectant.

17. A composition according to claim 1, further comprising a dry-feel modifier.

18. A composition according to claim 1, further comprising a waterproofing agent.

19. A composition according to claim 1, further comprising an antimicrobial preservative.

20. A composition according to claim 1, further comprising an antioxidant.

21. A composition according to claim 1, further comprising a cheating agent.

22. A composition according to claim 1, further comprising one or more of an adjuvant, a propellant, a leveling agent, and a dispenser.

23. A composition according to claim 1, further comprising a fragrance.

24. A method of forming a colored sunscreen composition, comprising the steps of:

mixing a sunscreen active with water and an oil-soluble dye to impart a color, other than white, to the composition, wherein application of the composition to the skin imparts the color to the skin and wherein the color substantially disappears when the composition is rubbed and/or spread onto the skin.

25. A colored composition for application to human skin, comprising:

an oil-soluble dye to impart a color, other than white, to the composition;

and water, wherein application of the composition to the skin imparts the color to the skin and wherein the color substantially disappears when the composition is rubbed and/or spread onto the skin.

* * * * *